(12) United States Patent
Cha et al.

(10) Patent No.: US 10,004,419 B2
(45) Date of Patent: Jun. 26, 2018

(54) ELECTRODE FOR MEASURING LIVING BODY SIGNAL

(71) Applicant: InBody Co., Ltd., Seoul (KR)

(72) Inventors: Ki Chul Cha, Seoul (KR); Chang Su Ji, Gyeonggi-do (KR)

(73) Assignee: InBody Co., Ltd., Seoul (KR)

( * ) Notice: Subject to any disclaimer, the term of this patent is extended or adjusted under 35 U.S.C. 154(b) by 339 days.

(21) Appl. No.: 14/855,131

(22) Filed: Sep. 15, 2015

(65) Prior Publication Data

US 2016/0120475 A1  May 5, 2016

(30) Foreign Application Priority Data

Oct. 30, 2014  (KR) .................. 10-2014-0149475

(51) Int. Cl.
| | | |
|---|---|---|
| *A61B 5/0478* | (2006.01) | |
| *A61B 5/00* | (2006.01) | |
| *A61B 5/04* | (2006.01) | |
| *A61B 5/01* | (2006.01) | |
| *A61B 5/0402* | (2006.01) | |
| *A61B 5/0476* | (2006.01) | |
| *A61B 5/0488* | (2006.01) | |
| *A61B 5/053* | (2006.01) | |

(52) U.S. Cl.
CPC .............. *A61B 5/0478* (2013.01); *A61B 5/04* (2013.01); *A61B 5/6814* (2013.01); *A61B 5/6838* (2013.01); *A61B 5/6839* (2013.01); *A61B 5/6868* (2013.01); *A61B 5/01* (2013.01); *A61B 5/0402* (2013.01); *A61B 5/0476* (2013.01); *A61B 5/0488* (2013.01); *A61B 5/0533* (2013.01); *A61B 2562/0209* (2013.01)

(58) Field of Classification Search
CPC ..................................................... A61B 5/0478
USPC .................................................. 600/378, 383
See application file for complete search history.

(56) References Cited

U.S. PATENT DOCUMENTS

| | | | | |
|---|---|---|---|---|
| 3,120,227 A | * | 2/1964 | Hunter, Jr. ........... | A61B 5/0444 600/511 |
| 3,989,038 A | * | 11/1976 | Neward ............... | A61B 5/0416 600/376 |
| 4,080,961 A | * | 3/1978 | Eaton ................... | A61B 5/0448 600/376 |
| 4,177,818 A | * | 12/1979 | De Pedro ............. | A61N 1/0587 607/130 |
| 4,254,764 A | * | 3/1981 | Neward ............... | A61B 5/4362 600/376 |
| 4,644,956 A | * | 2/1987 | Morgenstern ........ | A61B 5/0416 600/376 |
| 5,375,594 A | * | 12/1994 | Cueva ................... | A61B 5/042 600/377 |
| 6,308,105 B1 | * | 10/2001 | Duysens .............. | A61N 1/0551 607/116 |

* cited by examiner

*Primary Examiner* — Lee S Cohen
(74) *Attorney, Agent, or Firm* — Marshall, Gerstein & Borun LLP

(57) ABSTRACT

An electrode device for measuring a living body is herein disclosed. The electrode device for measuring a living body signal includes a body comprising a handle part and a tongs part, the body elastically moving by an external force, an electrode part comprising needles disposed on inner surfaces of the tongs part to face each other, and a wire part connected to one end of the electrode part for a connection with a measuring device.

13 Claims, 18 Drawing Sheets (a)

(b)

(a)

(b)

(a)

(b)

(a)

(b)

(a)

(b)

(a)

(b)

(a)

(b)

ELECTRODE FOR MEASURING LIVING BODY SIGNAL

CROSS-REFERENCE TO RELATED APPLICATIONS

A claim for priority under 35 U.S.C. § 119 is made to Korean Patent Application No. 10-2014-0149475 filed Oct. 30, 2014, in the Korean Intellectual Property Office, the entire contents of which are hereby incorporated by reference.

BACKGROUND

Embodiments of the inventive concepts described herein relate to an electrode device, and more particularly, to an electrode device capable of measuring a living body signal with a simple electrode structure and transmitting electrical signals obtained from a living body without loss.

A body may be a type of a conductor and a large amount of micro-current may occur in the body. Accordingly, characteristics in the body are measured based on a result of detecting the micro-current from the body or detecting a change in a current on external stimulation. In general, the above-described manner is used to measure electrocardiogram (ECG), electromyogram (EMG), electroencephalogram (EEG), skin resistance (e.g., galvanic skin response (GSR)), eyeball exercise (e.g., an electrooculogram (EOG)), body temperature, pulse rate, blood pressure, body movements, and the like, and an electrode for a living body is used to detect a change in a living body signal.

This electrode includes an electrode member which is formed of a conductive material and is disposed so as to be usually exposed to an outside. In addition, a sheet member includes an adhesive surface to allow the electrode member to adhere to a skin of the body and is disposed around the electrode member, and a snap projection is disposed on the electrode member so as to penetrate the sheet member and upwardly protrude. The snap projection is connected to a socket of a connection wire part connected to a signal processing module of a living body signal analysis device. Furthermore, an adhesive material of a gel state such as electrolyte is coated on the electrode member exposed to the outside to allow a contact with the skin to be maintained stably, and the relatively stable contact between the skin and the electrode member is maintained through the coated adhesive material.

However, the skin contains an outer skin layer including a horny layer of a skin barrier function, which prevents moisture, electrolyte, and the like from being outputted into an outside of the body and foreign substance from being inputted from the outside. For this reason, biological signals, such as the amount of current or a change in a current caused in a body part to be measured, are subjected to interference by a skin layer while passing through the skin layer, and thus, the biological signals are weakened or a noise occurs.

Accordingly, even though the adhesive material is interposed between the electrode member and the skin, a conventional electrode measures a signal generated from an outer skin layer upon measuring, thereby making it difficult to completely measure a living body signal generated in the body part as it is. In addition, the adhesive material, used to maintain a stable contact and to improve signal transmission between the electrode member and the skin, causes skin irritation even though an individual difference is when being in contact with the skin.

SUMMARY

Embodiments of the inventive concepts provide an electrode device for measuring a living body signal, capable of suppressing generation of noise by using an electrode structure of a simple tongs shape transmitting an electrical signal obtained from a living body without loss.

Embodiments of the inventive concepts provide an electrode device for measuring a living body signal, capable of quickly and easily measuring a living body signal of a desired portion without using an electrode glue or gel and measuring the living body signal through an electrode needle while wearing a cap for surgery.

One aspect of embodiments of the inventive concept is directed to provide an electrode device for measuring a living body signal, including a body comprising a handle part and a tongs part, the body elastically moving by an external force, an electrode part comprising needles disposed on inner surfaces of the tongs part to face each other, and a wire part connected to one end of the electrode part for a connection with a measuring device.

The living body signal may be measured from a scalp at a state where the electrode part is fixed to the scalp using a restoring force which is obtained after opening the tongs part of the body by the external force applied to the handle part.

The electrode part may be fixed to a living body using a restoring force which is obtained after opening the tongs part of the body by the external force applied to the handle part.

That the electrode part may be fixed to the living body by the restoring force is that the electrode part is inserted into an outer skin layer of the living body.

Opposite ends of the tongs part may be not touched with each other even though the external force is not applied to the handle part.

The needles of the electrode part may be disposed at opposite ends of the tongs part to face each other, and the needles may be fixed to a living body as the tongs part is closed.

The needles of the electrode part may be in contact with the living body in an angle, of less than 90 degrees.

The needles of the electrode part may be disposed on inner surfaces of the opposite ends of the tongs part to face each other, root portions of the needles may protrude outwardly from the opposite ends, and electrode members connecting the root portions may be formed such that the wire part is connected to each of the electrode members.

The wire part may connect the electrode members to obtain one electrode signal, or the electrode members may be respectively connected to a plurality of wire parts to obtain a plurality of electrode signals.

The needles, the electrode members, and the wire part may be integrated into one and are detached from or attached to the body.

The electrode part may include a plurality of needles formed sharply.

The electrode part may include a plurality of needles sharply formed, and root portions of the needles may be connected to each other.

The electrode part may be formed of sheet metal, a plurality of needles may be formed at one side of the electrode part so as to be fixed to a living body, and the other side thereof may be connected to the wire part.

One surface of each needle may be curved.

At least one protrusion part may be formed on an inner side of the handle part and limits a distance by which the tongs part is opened.

Curved portions may be formed at opposite ends of the body so as to be elastically curved in a side opposite to the electrode part, the electrode device may be disposed in an ejection apparatus at a state where the curved portions are pressurized, and the electrode device may be ejected to an outside of the ejection apparatus by an external force such that the electrode part is fixed to a living body by a restoring force of the curved portions.

Another aspect of embodiments of the inventive concept is directed to provide an electrode device for measuring a living body signal, including a body bent at least once to have a U-shape, one end thereof being extended, a handle part formed on one side of the one end of the body thus extended, and an electrode part formed on the other side of the one end of the body thus extended and acting as an electrode.

The one end of the body may be elastically bent when a tension acts at the handle part, and the electrode part may be fixed to a living body by a restoring force.

Another aspect of embodiments of the inventive concept is directed to provide an electrode device for measuring a living body signal, including a handle part of a tongs shape, a body connected to the handle part by a spring to have the tongs shape, and a needle-shaped electrode part formed on a bottom surface of one end portion of the body and operating as an electrode.

The electrode part may be fixed to a living body using a restoring force which is obtained after pressurizing the handle part and opening the one side of the body.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Below, embodiments of the inventive concept will be described in detail with reference to the attached drawings.

Figure 1:
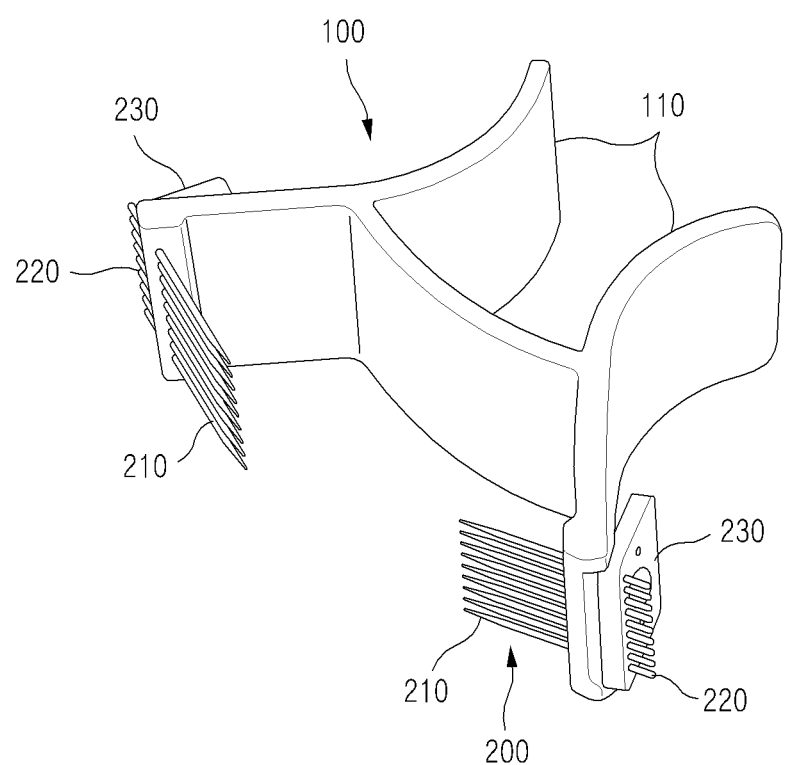
FIG. 1 is a perspective view illustrating an electrode device for measuring a living body signal according to an embodiment of the inventive concept.

FIG. 1 is a perspective view illustrating an electrode device for measuring a living body signal, according to an embodiment of the inventive concept.

Referring to FIG.1, an electrode device for measuring a living body signal may include a body 100 and an electrode part 200. In addition, a wire part (not illustrated) connected to a measuring device may be further included.

The body 100 may be implemented in the form of tongs which elastically moves by virtue of an external force. A handle part 110 may be formed at one side of the body 100, and a tongs part which moves according to movement of the handle part 110 may be formed at the other side thereof. In this case, opposite ends of the tongs part may not be touched with each other even though an external force is not applied to the handle part 110. This may allow the electrode part 200 to maintain a distance when the tongs part is opened by the external force applied. This may mean that the electrode part 200 inserted to a living body of a to-be-measured person maintains the distance. Therefore, a pain of the to-be-measured person may be reduced.

The electrode part 200 which operates as an electrode may include at least one or more needles and may be formed in a needle shape on inner surfaces of the tongs part so as to face each other. The electrode part 200 may include needles 210 that are disposed at opposite ends of the tongs part so as to face each other, and the needles 210 may be fixed to the living body as the tongs part of the body 100 is closed. In this case, the needles 210 of the electrode part 200 may be in contact with the living body in a predetermined angle, for example, of less than 90 degrees and may be fixed to the living body.

In addition, the electrode part 200 may include the needles 210 which are disposed on inner sides of the opposite ends of the tongs part so as to face each other, root portions 220 of the needles 210 may protrude outwardly, and an electrode member 230 connecting the root portions 220 may be formed. The electrode member 230 may include a printed circuit board (PCB) and may be connected to a measurement apparatus, such as a signal processor and the like, via a wire part.

Accordingly, the tongs part of the body 100 may be opened by the external force applied to the handle part 110, and the electrode part 200 may be fixed to the living body of the to-be-measured person by a restoring force. In this case, that the electrode part 200 is fixed to the living body of the to-be-measured person by the restoring force may mean that the electrode part 200 is inserted into an outer skin layer of the living body. The electrode part 200 may be fixed to a scalp of the to-be-measured person by a restoring force which is obtained after opening the tongs part of the body 100 by the external force applied to the handle part 110, thereby making it possible to measure a living body signal from the scalp.

With the above description, the electrode device for measuring the living body signal may be inserted into the outer skin layer of the body of the to-be-measured person, may collect the living body signal, and may measure electrocardiogram (ECG), electromyogram (EMG), electroencephalogram (EEG), skin resistance (e.g., galvanic skin response (GSR)), eyeball exercise (e.g., electrooculogram (EOG)), body temperature, and the like from the collected living body signal.

Figure 2:
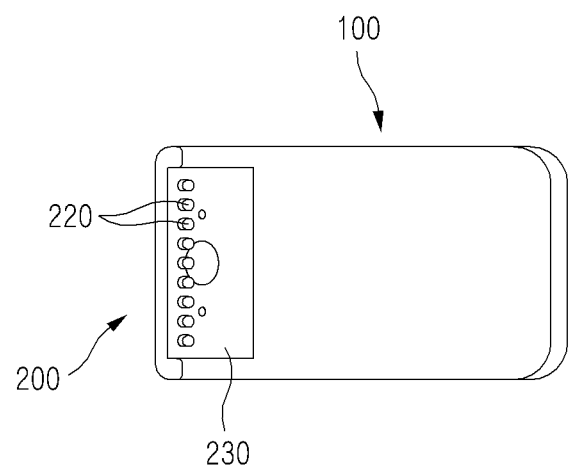
FIG. 2 a side view illustrating an electrode device for measuring a living body signal according to an embodiment of the inventive concept.

FIG. 2 is a side view illustrating an electrode device for measuring a living body signal, according to an embodiment of the inventive concept.

Referring to FIG. 2, the electrode device for measuring the living body signal may have the electrode part 200 formed at the tongs part of the body 100 and the electrode part 200 may include at least one or more needles acting as an electrode and the electrode member 230.

In other words, the electrode part 200 may be formed at the tongs part, that is, at opposite ends of the body 100. Needles may be disposed at the opposite ends of the tongs part so as to face each other, thereby making it possible for the needles to be fixed to a living body when the tongs part is closed. In this case, the needles of the electrode part 200 may be in contact with the living body in the angle, for example, in less than 90 degrees and then may be fixed thereto.

In addition, the needles of the electrode part 200 may be disposed on inner surfaces of the opposite ends of the tongs part to face each other, the root portions 220 of the needles may protrude outwardly, and the electrode member 230 connecting the root portions 220 may be further formed. The electrode member 230 may be connected to the measurement apparatus such as the signal processor, and the like, via a wire part.

Furthermore, the needles of the electrode part 200, the electrode member 230, and the wire part may be optionally integrated so as to be removed from the body 100 or the tongs part of the body 100, thereby making it possible to easily replace the module independently, if necessary.

Figure 3:
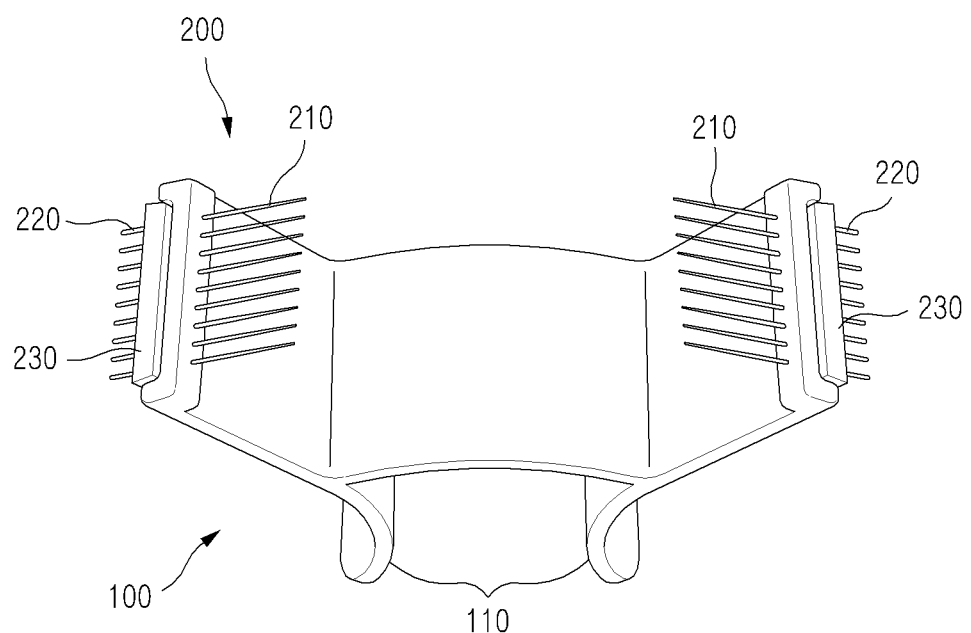
FIG. 3 is a diagram illustrating an electrode part of an electrode device for measuring a living body signal according to an embodiment of the inventive concept.

FIG. 3 is a diagram illustrating an electrode part of an electrode device for measuring a living body signal, according to an embodiment of the inventive concept.

Referring to FIG. 3, the electrode device for measuring the living body signal may measure the living body signal as the electrode part 200 is fixed to the living body of the to-be-measured person by a restoring force which is obtained after pressurizing the handle part 110 of the body 100 to open the tongs-shaped body 100. In this case, that the electrode part 200 is fixed to the living body of the to-be-measured person by the restoring force may mean that the electrode part 200 is inserted into an outer skin layer of the living body and then is fixed thereto. For example, the tongs part of the body 100 may be opened by an external force applied to the handle part 110, and the electrode part 200 may be fixed to a scalp of the to-be-measured person by the restoring force, thereby making it possible to measure a living body signal from the scalp.

The electrode part 200 may include at least one or more needles which operate as an electrode, and the needles may be formed at the tongs part, for example, at the opposite ends of the body 100. Furthermore, the needles 210 of the electrode part 200 may be disposed at the opposite ends of the tongs part to face each other and may be fixed to the living body when the tongs part is closed.

In this case, a shape of the electrode part 200 may not be limited to this disclosure. For example, the needles 210 may include a plurality of sharp needles, and the electrode part 200 may be formed such that the needles 210 are formed sharply and the root portions 220 of the needles are connected to each other. Various modifications or changes on the needles 210 may be possible if the needles 210 are formed sharply to be inserted in the living body.

Furthermore, in the electrode part 200, a length of the needles 210 may be determined such that the needles 210 are inserted into the outer skin layer of the living body.

Figure 4:
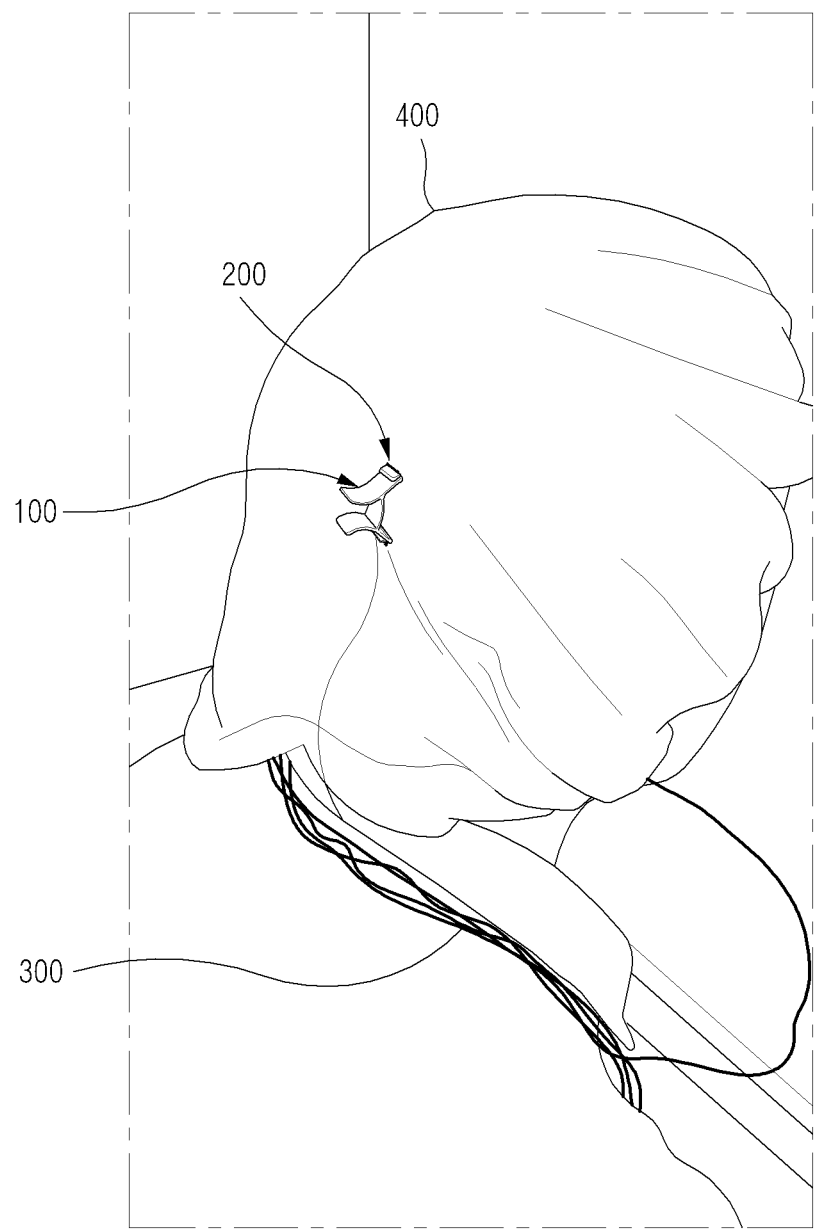
FIG. 4 is a diagram illustrating an application of an electrode device for measuring a living body signal according to an embodiment of the inventive concept.

FIG. 4 is a diagram illustrating an application of an electrode device for measuring a living body signal, according to an embodiment of the inventive concept.

Referring to FIG. 4, an embodiment of the inventive concept is exemplified as the electrode device for measuring the living body signal measures a brain-wave signal among living body signals. The electrode device may measure a living body signal by fixing the electrode part 200 to a head of a to-be-measured person using a restoring force which is obtained after pressurizing the handle part 110 of the electrode device and opening the tongs part.

In this case, a wire part 300 (e.g., a dedicated wire) may be further included which connects the electrode part 200 of the electrode device to the measurement apparatus such as a signal processor, and the like.

In addition, the electrode device for measuring the living body signal may measure the brain-wave signal via an electrode needle even when a to-be-measured person wears a cap 400 for surgery, and thus, the electrode device may be useful for a surgical situation.

One electrode device may be used to measure one living body signal, and two or more electrode devices may be connected to perform a required function, if necessary. As such, the electrode device for measuring the living body signal may be attached to a body to be measured and may measure electrocardiogram (ECG), electromyogram (EMG), electroencephalogram (EEG), skin resistance (e.g., a galvanic skin response (GSR)), eyeball movement (e.g., an electrooculogram (EOG)), body temperature, and the like from the collected living body signals.

In this case, a method for measuring the living body signal may include measuring a living body signal obtained from the electrode device at a state where the measurement apparatus such as the signal processor and the like is connected to an electrode member by the wire unit 300. In this case, the measurement apparatus may include, for example, an analog signal processing unit, an A/D converter, a digital signal processor, and a wired/wireless transmitter module. The analog signal processing unit may amplify and filter micro electricity of the body transmitted from the electrode member as a terminal, for example, an analog signal and may transmit the amplified and filtered signal to the A/D converter. After the A/D converter converts the transmitted analog signal into a digital signal, the digital signal processor may process the converted digital signal based on a method programmed. In addition, the processing result may be transmitted into an external system via the wired/wireless transmitter module. Alternatively, the processing result may be stored in an internal memory.

Figure 5:
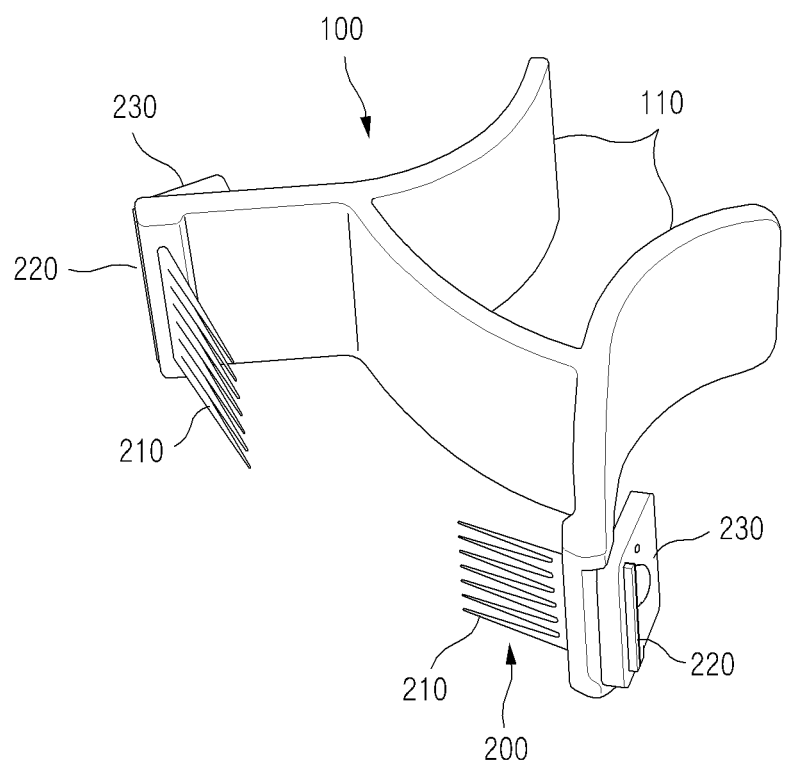
FIG. 5 is a perspective view illustrating an electrode device for measuring a living body signal according to another embodiment of the inventive concept.

FIG. 5 is a perspective view illustrating an electrode device for measuring a living body signal, according to another embodiment of the inventive concept.

Referring to FIG. 5, the electrode device for measuring the living body signal may include the body 100 and the electrode part 200. In this case, a description duplicated with the electrode device described with reference to FIGS. 1 to 4 may be omitted, and a brief description will be given.

The body 100 may be implemented in a tongs shape. The handle part 110 may be disposed at one side of the body 100, and the tongs part which moves according to a movement of the handle part 110 may be disposed at the other side thereof.

The electrode part 200 which operates as an electrode may be implemented with at least one or more needles, and the needles 210 may be disposed at opposite ends of the tongs part of the body 100 to face each other. Accordingly, when the tongs part is closed, the needles 210 may be fixed to a living body. In this case, the electrode part 200 may include the plurality of needles 210 and the root part 220 connecting the plurality of needles into one. In addition, the electrode member 230 may be further included.

As such, a shape of the electrode part 200 may not be limited to this disclosure, the plurality of needles 210 may be sharply formed, and needles of the root part 220 may be connected to each other. The plurality of needles 210 may be inserted into an outer skin layer of the living body, thereby making it possible to measure the living body signal. Meanwhile, in the electrode part 200, a length of the needles 210 may be determined such that the needles 210 are inserted into the outer skin layer of the living body.

Figure 6:
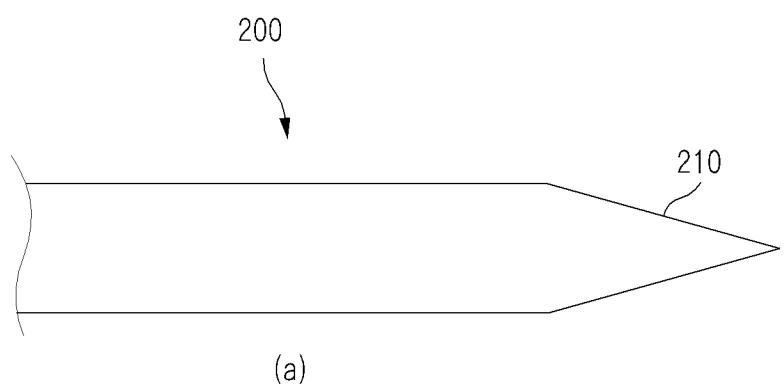
FIG. 6 is a diagram illustrating an electrode part according to an embodiment of the inventive concept.
Figure 6:
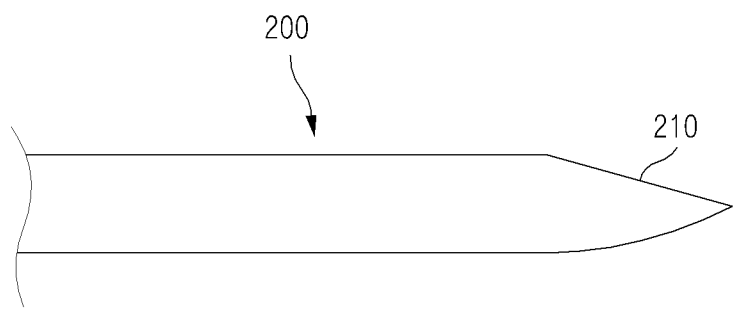

FIG. 6 is a diagram illustrating an electrode part according to an embodiment of the inventive concept.

Referring to FIG. 6A, the needle 210 of the electrode part 200 may be implemented in the form of a general needle and may be illustrated as being implemented in the form of a straight line in a cross-sectional view.

Referring to FIG. 6B, in the electrode part 200, one surface of the needle 210 may be curved, thereby reducing a pain of a to-be-measured person when the needle 210 is fixed to a living body by curvature. In other words, in the cross-sectional view, one side of the needle 210 may be curved, and the other side thereof may be implemented in the form of a straight line. Alternatively, opposite sides of the needle 210 may be curved such that curvatures thereof are different from each other.

Figure 7:
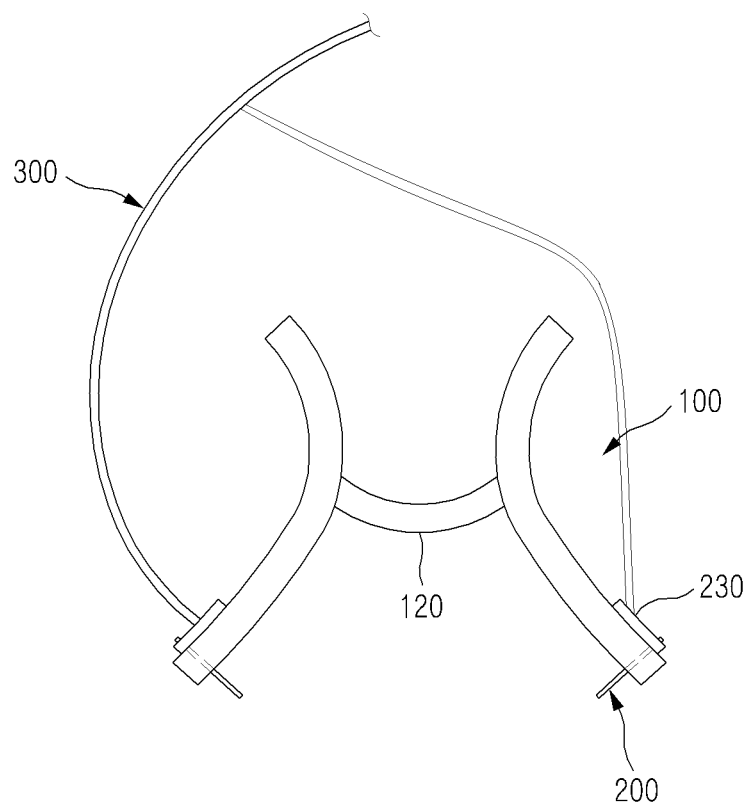
FIG. 7 is a top plain view illustrating an electrode device for measuring a living body signal according to an embodiment of the inventive concept.

FIG. 7 is a top plain view illustrating an electrode device for measuring a living body signal, according to an embodiment of the inventive concept.

Figure 8:
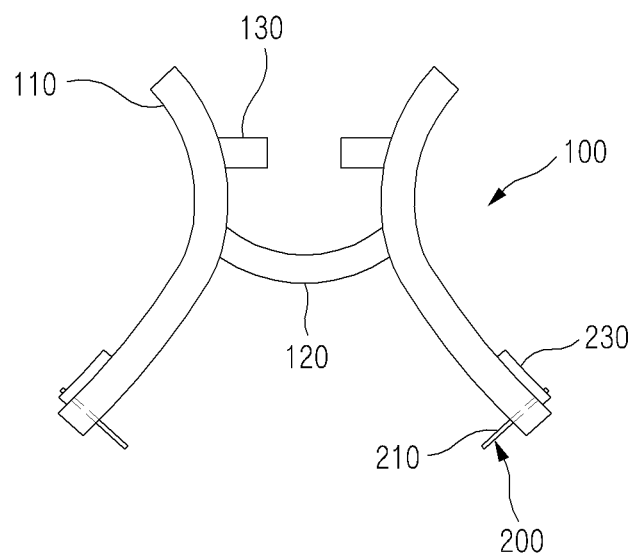
FIGS. 8 to 18 are diagrams illustrating an electrode device for measuring a living body signal according to another embodiment of the inventive concept.

FIG. 8 is a diagram illustrating an electrode device for measuring a living body signal, according to another embodiment of the inventive concept.

Referring to FIG. 7, the electrode device for measuring the living body signal may include the body 100 and the electrode part 200.

The body 100 may be implemented in the form of tongs. The handle part 110 may be formed at one side of the body, and a tongs part which moves according to movement of the handle part 110 may be formed at the other side thereof. Furthermore, a connecting part 120 may be formed which connects two handle parts of the body 100. In this case, the connecting part 120 may be integrated with the body 100, or may be formed independently of the body 100. The connecting part 120 may be implemented with a spring or the like.

The electrode part 200 may include at least one or more needles operating as an electrode, and a plurality of needles may be formed at the tongs part, that is, at opposite ends of the body 100. Furthermore, the electrode part 200 may include needles 210 which are disposed at opposite ends of the tongs part so as to face each other, and the needles 210 may be fixed to the living body as the tongs part of the body 100 is closed. In addition, the electrode member 230 may be formed at the root portions 220 of the electrode part 200 and may be connected to a wire part 300, thereby making it possible to measure the living body signal.

Referring to FIG. 8, at least one or more protrusion parts 130 may be formed on an inner side of the handle part 110 and may limit a distance by which the tongs part is opened. In other words, in the case of pressurizing the handle part 110, a pressure may be limited by the protrusion parts 130, and thus, it is possible to limit a distance by which the tongs part is maximally opened.

Figure 9:
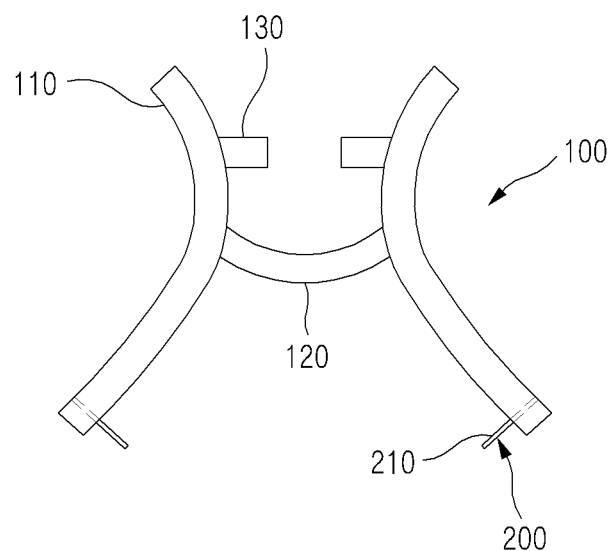

FIG. 9 is a diagram illustrating an electrode device for measuring a living body signal, according to another embodiment of the inventive concept.

Figure 10:
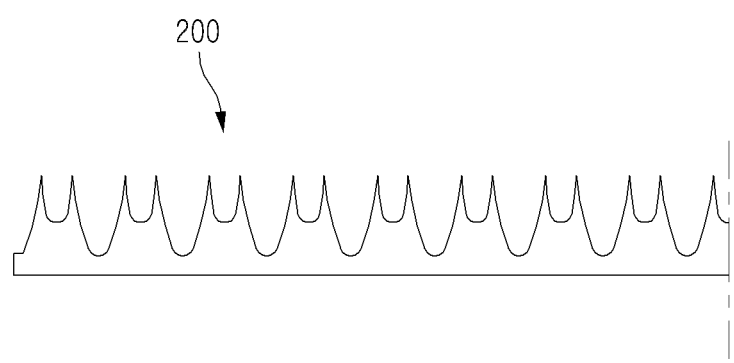

FIG. 10 is a diagram illustrating an electrode part formed of a sheet metal, according to another embodiment of the inventive concept.

Referring to FIG. 9, the electrode device for measuring the living body signal may include the body 100 and the electrode part 200. The electrode part 200 may be formed at the tongs part of the body 100.

The electrode part 200 may be formed of the sheet metal. In this case, since a wire part is connected to the sheet metal to measure the living body signal, an electrode member including a separate PCB may not be required, and thus, the electrode part 200 may be implemented by a simple method.

Referring to FIG. 10, the electrode part 200 may be formed of the sheet metal, and a plurality of needles may be formed by cutting end portions thereof sharply. This may allow the electrode part 200 to be fixed to the living body. In this case, as illustrated in FIG. 10, since the needles are obliquely sheared so as to become thinner and sharper, the electrode part 200 may be easily inserted into an outer skin layer of a living body without causing a pain of the to-be-measured person.

Figure 11:
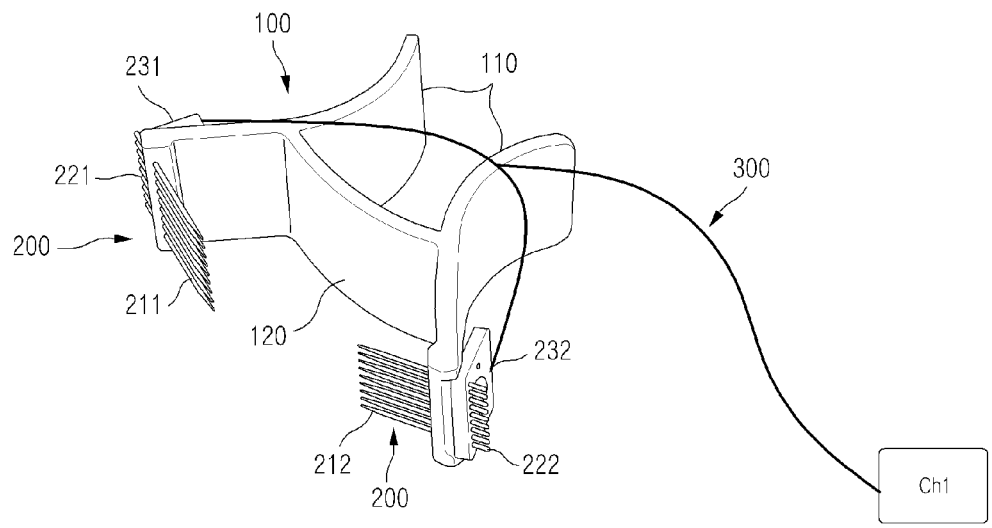
Figure 11:
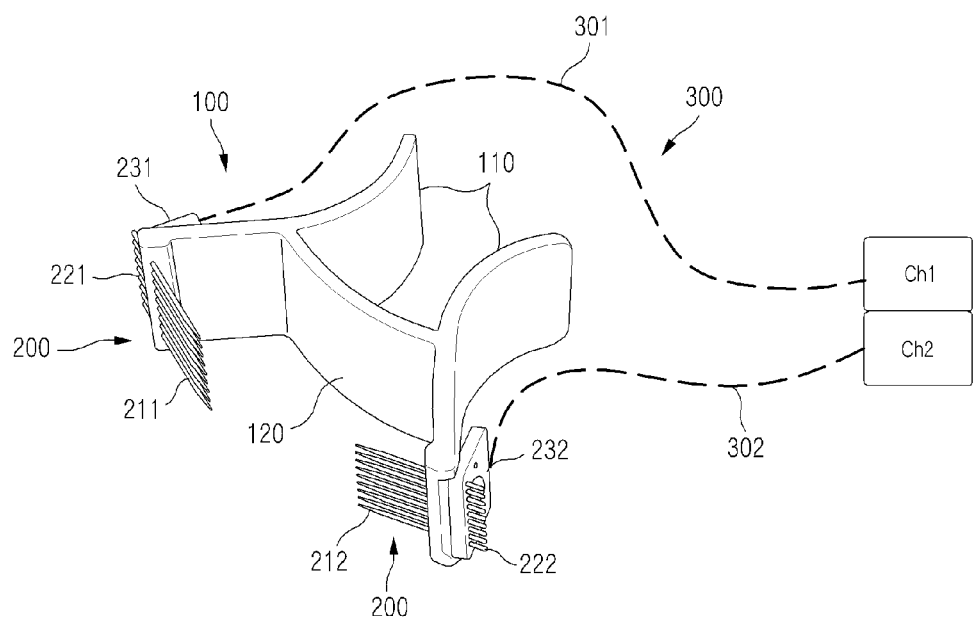

FIG. 11 is a diagram illustrating a wire part for measuring a living body signal, according to another embodiment of the inventive concept.

Referring to FIG. 11A, the wire part 300 may be connected to each of electrode members 221 and 222 and may obtain one electrode signal.

In other words, two electrode parts 200 which are formed at opposite ends of the body 100 may be connected to the wire part 300 based on a use purpose or a spatial precision and accuracy of the living body signal, and thus, one electrode signal may be obtained.

Referring to FIG. 11B, wire parts 301 and 302 may be connected to the electrode members 221 and 222, respectively, and thus, a plurality of electrode signals may be obtained.

In other words, two electrode parts 200 which are formed at opposite ends of the body 100 may be respectively connected to the wire parts 301 and 302 based on a use purpose or a spatial precision and accuracy of the living body signal, and thus, the plurality of electrode signals may be obtained. Therefore, each of the electrode parts 200 may be used as an individual electrode.

Furthermore, a standardized electrode placement or non-standardized electrode placement may be possible according to adjusting a length of the connection part 120 in the body 100.

Below, the inventive concept will be more fully described with respect to FIGS. 1 to 11.

An electrode device for measuring a living body signal, according to an exemplary embodiment of the inventive concept may be fixed to an outer skin layer of the living body of a to-be-measured person using the restoring force which is obtained after pressurizing the handle part 110 of the body of the electrode device and opening the body of the tongs shape. Accordingly, the needles of the electrode part may be inserted into the outer skin layer of the living body of the to-be-measured person by the restoring force, thereby making it possible to measure the living body signal.

In this case, an electrode member connecting a plurality of needles may be connected to a measurement apparatus via the wire part to allow the measurement apparatus to collect the living body signal. Therefore, it may be possible to measure electrocardiogram (ECG), electromyogram (EMG), electroencephalogram (EEG), skin resistance (e.g., galvanic skin response (GSR)), eyeball exercise (e.g., an electrooculogram (EOG)), body temperature, and the like from the collected living body signal.

As described above, an electrode device according to an exemplary embodiment of the inventive concept may be an electrode of a form in which thin needles are fixed at opposite ends of the tongs-shaped body 100, and may measure a living body signal by fixing the needles to a living body of a to-be-measured person using a restoring force which is obtained after pressurizing the handle part 110 and opening the tongs part of the body 100.

Figure 12:
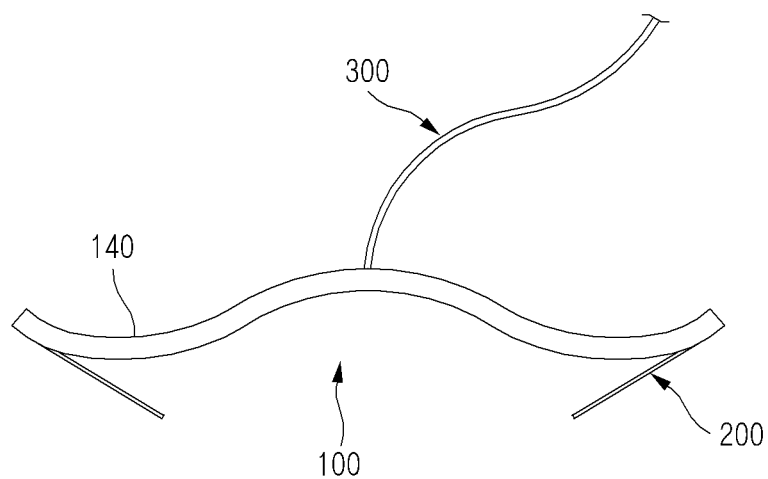

FIG. 12 is a diagram illustrating an electrode device for measuring a living body signal, according to another embodiment of the inventive concept.

Referring to FIG. 12, the electrode device for measuring the living body signal may include the body 100 and the electrode part 200.

The body 100 may be formed of a plate spring such as a sheet metal and the like, and a curved portion 140 may be formed by bending. Furthermore, the electrode part 200 in which a needle is formed may be formed at one side of the curved portion 140.

In this case, since the entire body 100 is formed of a conductive material, the wire part 300 may be directly connected to the body 100 without using a separate electrode member 100, and thus, it may be possible to measure the living body signal. As such, the electrode device for measuring the living body signal may be implemented with one piece, and thus, it may be easily and economically produced.

Figure 13:
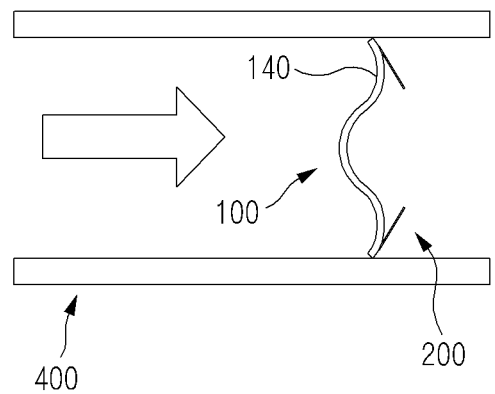
Figure 13:
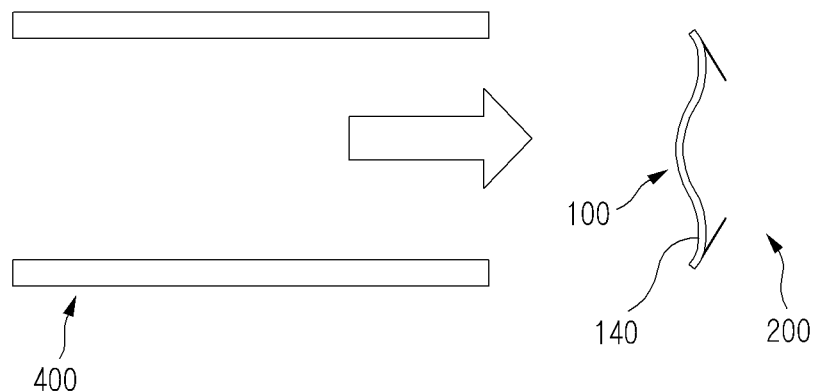

FIG. 13 is a diagram illustrating an electrode device for measuring a living body signal, outputted from an ejection apparatus, according to another embodiment of the inventive concept.

Referring to FIG. 13A, the electrode device for measuring the living body signal described in FIG. 12 may be fixed to a living body when outputted from the ejection apparatus.

In other words, in the electrode device for measuring the living body signal, the curved portions 140 which are elastically curved into a side opposite to the electrode part 200 may be formed at opposite ends of the body 100. Furthermore, the curved portion 140 may be disposed in the ejection apparatus 400 such that it is bent by a pressure applied.

In this case, the ejection apparatus 400 may be an apparatus which allows the electrode device, pressurized in the ejection apparatus 400, to be pushed out toward an outside by an external force in a manner similar to a clamp clip dispenser.

Referring to FIG. 13B, the electrode device for measuring the living body signal may be ejected to the outside by the external force acting on the ejection apparatus 400 such that the curved portion 140 being pressurized is unbent by the restoring force, and thus, the electrode part 200 may be fixed to the living body.

By using an instrument such as the ejection apparatus and the like, the electrode device may be attached to the living body by a constant force all the time.

Figure 14:
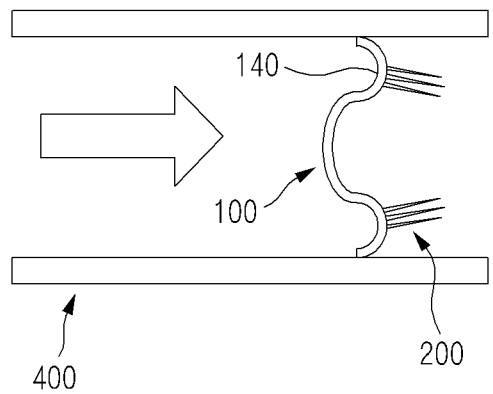
Figure 14:
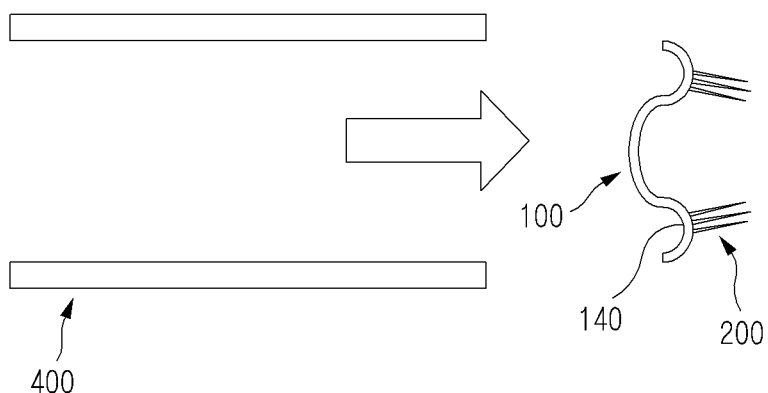

FIG. 14 is a diagram illustrating an electrode device for measuring a living body signal, outputted from an ejection apparatus, according to another embodiment of the inventive concept.

Referring to FIG. 14A, like FIG. 13, the electrode device for measuring the living body signal may be ejected from the ejection apparatus and may be fixed to the living body.

The electrode device for measuring the living body signal may include the body 100 and the electrode part 200.

The curved portion 140 of the body 100 may be formed to be bent at opposite ends of the body 100. The curved portion 140 may have elasticity and may be more bent by the pressure applied when the curved potion 140 is disposed in the ejection 400.

The electrode part 200 may be formed on a surface of the curved portion 140 facing an outlet of the ejection apparatus and may include a plurality of needles. Furthermore, the electrode part 200 may include an electrode member connecting the plurality of needles. The electrode member and a wire part may be connected to measure the living body signal.

Referring to FIG. 14B, the electrode device for measuring the living body signal may be ejected to the outside by the external force acting on the ejection apparatus 400 such that the curved portion 140 being pressurized is unbent by the restoring force, and thus, the electrode part 200 may be fixed to the living body.

Figure 15:
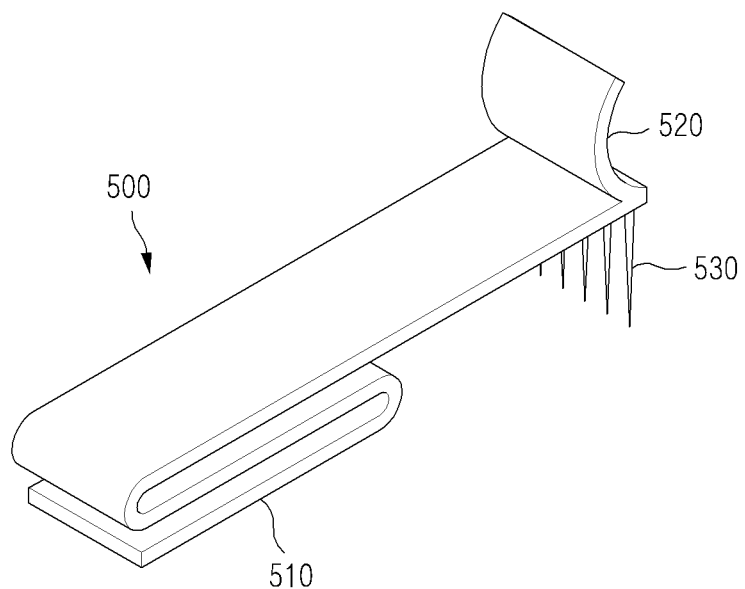

FIG. 15 is a perspective view illustrating an electrode device for measuring a living body signal, according to another embodiment of the inventive concept.

Figure 16:
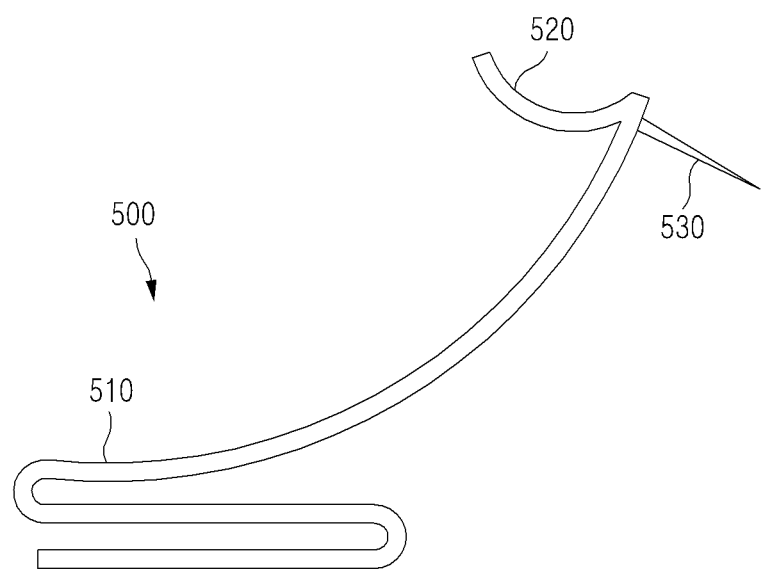
Figure 16:
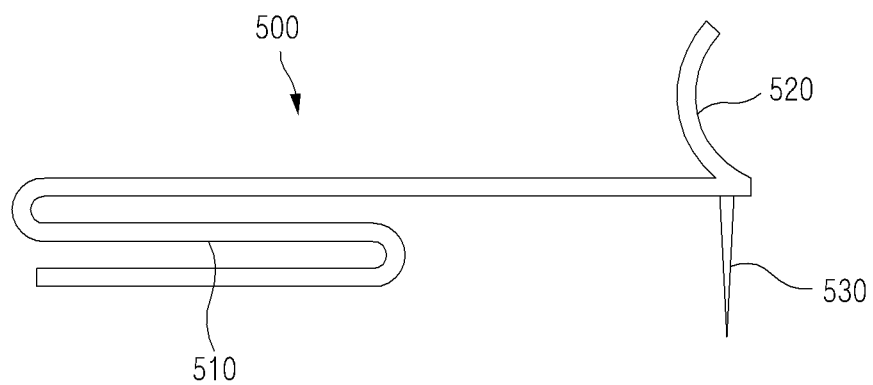

FIG. 16 is a side view illustrating an electrode device for measuring a living body signal, according to another embodiment of the inventive concept.

Referring to FIG. 15, the electrode device 500 for measuring the living body signal may include a body 510, a handle part 520, and an electrode part 530.

The body 510 may be bent at least once in a U-shape, and one end of the body 510 may be extended. Here, the body 510 may not be limited to the U-shape. For example, the body 510 may be formed in a U-shape or S-shape. A space may be formed by bending the body 510, and the body 510 may be fixed to hairs, a cap for surgery, or the like using the space.

The handle part 520 may be formed on one side of the one end of the body extended.

A electrode part 530 may operate as an electrode and may be formed on the other side of the one end of the body extended.

Referring to FIG. 16, in the body 510 of the electrode device 500 for measuring the living body signal, as tension acts at the handle part 520, the one end of the body 510 extended may be elastically bent, and thus, the electrode part 530 may be fixed to the living body by a restoring force.

A tongs shape may be slightly modified to have a fixing part of a clip shape. After fixing the electrode device 500 using the fixing part, the electrode part 530 as an electrode may be attached to the living body, the hairs, or the like using the handle part 520. That is, the body 510 with a clip or tongs shape may be attached to the hairs or a cap for surgery, and the electrode part 530 may be fixed to the living body, the hairs, or the like using the restoring force obtained after upwardly pulling and releasing the handle part 520.

Figure 17:
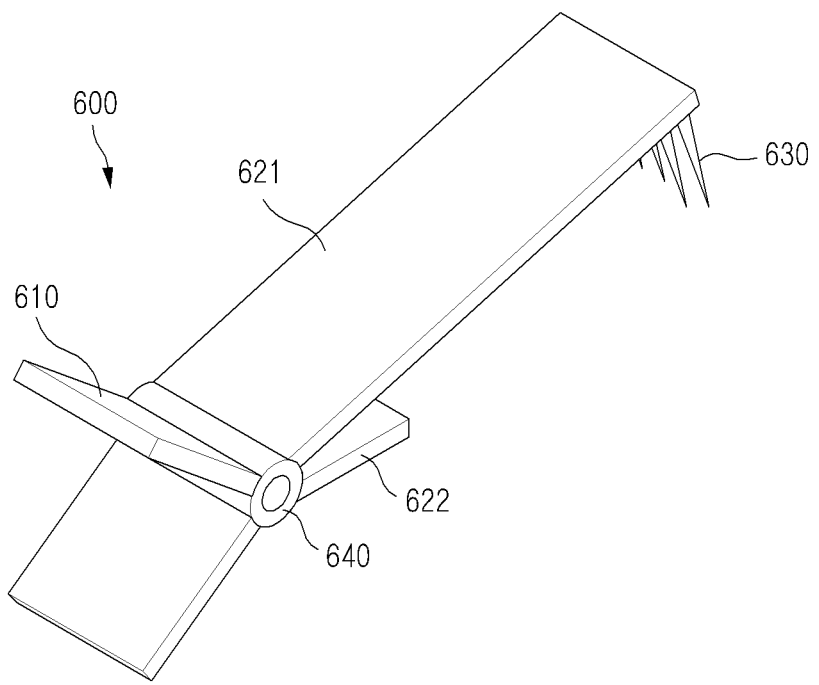

FIG. 17 is a perspective view illustrating an electrode device for measuring a living body signal, according to another embodiment of the inventive concept.

Figure 18:
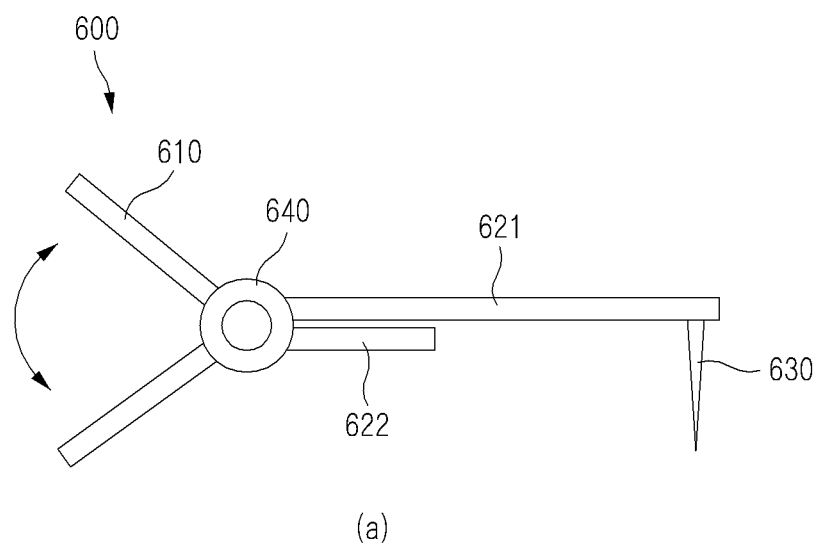
Figure 18:
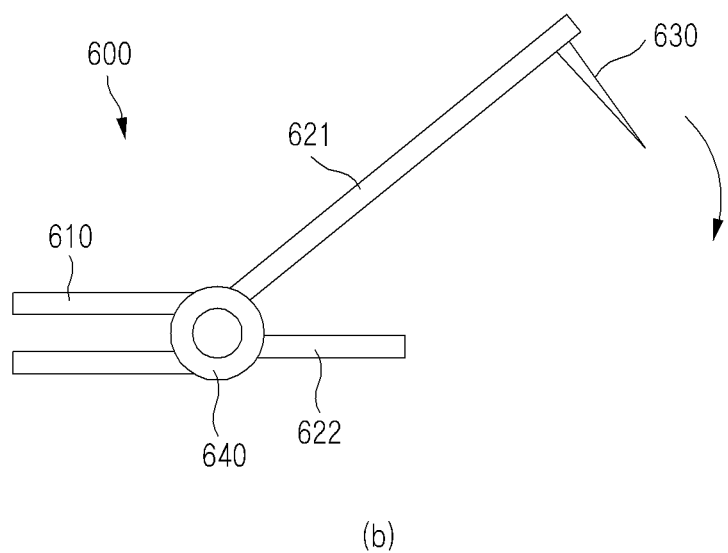

FIG. 18 is a side view illustrating an electrode device for measuring a living body signal, according to another embodiment of the inventive concept.

Referring to FIG. 17, the electrode device 600 for measuring the living body signal may include a handle part 610, a body (621, 622), and an electrode part 630.

The handle part 610 may be formed in a tongs shape.

The body (621, 622) may be connected by the handle part 610 and a spring 640 and may form the tongs shape.

The electrode part 630 may operate as an electrode and may be formed on one side 621 of the body (621, 622).

Referring to FIG. 18, in the body (621, 622) of the electrode device 600 for measuring the living body signal, the one side 621 of the body (621, 622) may be opened by pressurizing the handle part 610 and the electrode part 630 may be fixed to the living body by a restoring force.

In other words, in the case of pressurizing the handle part 610, a portion 621 of the body which the electrode part 630 as an electrode is attached to may be opened. In the case of releasing the handle part 610 at a state where the body 621 is opened, a tongs handle may be released after hairs or a cap for surgery is pushed and fixed by the body 622 where the electrode part is not formed. That is, a portion where the electrode part 630 is attached may be downwardly pulled by a restoring force of a spring 640, thereby making it possible for the electrode part 630 to be fixed to the living body.

As such, conventionally, glue or gel for an electrode may be coated on his/her head to allow an electrode device to be in contact with a living body. This manner may cause the following inconveniences: fixing one's hair to attach the electrode to a scalp and consuming a lot of time for living body measurement. Meanwhile, because the glue for the electrode is hard to remove, a to-be-measured person may feel an irritation from his/her hair or scalp and have a skin trouble after measurement.

Thus, an electrode device according to an exemplary embodiment of the inventive concept may quickly and easily measure a living body signal such as a brain wave of a desired portion without using the glue or gel. Especially, since it is possible to measure a brain wave signal through an electrode needle even while a to-be-measured person wears a surgical cap, the electrode device may be useful in surgical situations.

Although embodiments have been described by specific examples and drawings as described above, those of ordinary skill in the art that various modifications, additions and substitutions are possible from the above description. For example, the described techniques are performed in a different order with methods described, and/or although the system, architecture, device, and circuit components such as the methods described be coupled/combined with the other embodiment, or replaced/substituted by other components or equivalents, suitable results may be achieved.

According to an exemplary embodiment of the inventive concept, an electrode device for measuring a living body signal may be capable of suppressing generation of noise by using an electrode structure of a simple tongs shape transmitting an electrical signal obtained from a living body without loss.

According to an exemplary embodiment of the inventive concept, an electrode device for measuring a living body signal may be capable of quickly and easily measuring a living body signal of a desired portion without using an electrode glue or gel and measuring the living body signal through an electrode needle while wearing a cap for surgery.

Therefore, other implementations, other embodiments and equivalent things and claims may be within the scope of the claims to be described later.

What is claimed is:

1. An electrode device for measuring a living body signal, comprising:
    a body comprising a handle part and a tongs part, the body elastically moving by an external force;
    an electrode part comprising needles disposed on inner surfaces of the tongs part to face each other, wherein the needles of the electrode part are disposed on inner surfaces at opposite ends of the tongs part to face each other, such that the needles are fixed to a living body as the tongs part is closed, wherein root portions of the needles protrude outwardly from the opposite ends; and
    a wire part connected to one end of the electrode part for a connection with a measuring device, wherein the wire part is connected to the one end of the electrode part via a connection of the wire to a first electrode member which connects the root portions of the needles at a first opposite end of the opposite ends.

2. The electrode device of claim 1, wherein the electrode part is arranged to affix to a scalp using a restoring force obtainable by opening the tongs part of the body by the external force applied to the handle part.

3. The electrode device of claim 1, wherein the electrode part is arranged to affix to a living body via a restoring force obtainable by opening the tongs part of the body by the external force applied to the handle part.

4. The electrode device of claim 3, wherein the electrode part is arranged to affix to an outer skin layer of the living body by the restoring force.

5. The electrode device of claim 1, wherein opposite ends of the tongs part are not touched with each other even though the external force is not applied to the handle part.

6. The electrode device of claim 1, wherein the needles of the electrode part are arranged to contact the living body in an angle of less than 90 degrees as the tongs part is closed.

7. The electrode device of claim 1, wherein the wire part is further connected to a second end of the electrode part via a connection of the wire to a second electrode member connecting the root portions of the needles at a second opposite end of the opposite ends.

8. The electrode device of claim 7, wherein the wire part connects the electrode members to obtain one electrode signal, or the electrode members are respectively connected to a plurality of wire parts to obtain a plurality of electrode signals.

9. The electrode device of claim 7, wherein the needles, the electrode members, and the wire part are integrated into one and are detached from or attached to the body.

10. The electrode device of claim 1, wherein the electrode part comprises a plurality of needles formed sharply.

11. The electrode device of claim 1, wherein the electrode part comprises a plurality of needles sharply formed, and
    wherein root portions of the needles are connected to each other.

12. The electrode device of claim 1, wherein the electrode part is formed of sheet metal, and a plurality of needles are formed at one side of the electrode part so as to be fixed to a living body, and the other side thereof is connected to the wire part.

13. The electrode device of claim 1, wherein one surface of each needle is curved.

* * * * *